United States Patent [19]

Caslavsky et al.

[11] 4,353,892

[45] Oct. 12, 1982

[54] FLUORIDE PREPARATIONS CONTAINING SURFACE-ACTIVE AGENTS

[75] Inventors: Vera B. Caslavsky, Lexington; Poul Gron, Needham, both of Mass.

[73] Assignee: Forsyth Dental Infirmary for Children, Boston, Mass.

[21] Appl. No.: 292,496

[22] Filed: Aug. 13, 1981

[51] Int. Cl.$^3$ .............................................. A61K 7/18
[52] U.S. Cl. ........................................ 424/52; 424/48; 424/49; 424/54; 424/57; 424/151
[58] Field of Search ............................ 424/52, 57, 151

[56] References Cited

U.S. PATENT DOCUMENTS

| | | | |
|---|---|---|---|
| 2,829,086 | 4/1958 | Kirschenbauer | 424/52 |
| 2,913,373 | 11/1959 | Weisz et al. | 424/52 |
| 2,955,985 | 10/1960 | Kuna | 424/52 |
| 3,282,792 | 11/1966 | Fiscella | 424/52 |
| 3,975,514 | 8/1976 | Weisz | 424/52 |
| 4,078,053 | 3/1978 | De Paola | 424/52 |
| 4,083,955 | 4/1978 | Grabenstetter | 424/52 |
| 4,108,980 | 8/1978 | Duff | 424/52 |
| 4,130,636 | 12/1978 | Tomlinson | 424/52 |
| 4,170,636 | 10/1979 | Engel et al. | 424/52 |
| 4,243,658 | 1/1981 | Chang | 424/52 |

*Primary Examiner*—Shep K. Rose
*Attorney, Agent, or Firm*—Richard P. Crowley

[57] ABSTRACT

A dental-caries-inhibiting composition, such as toothpaste, mouthwash, or solution for profession application to teeth, which composition comprises a caries-inhibiting amount; for example, 50 to 30000 ppm, of a soluble fluoride and a surfactant having a perfluoroalkyl group in an amount sufficient to increase the formation of fluorapatite from enamel-fluoride interactions.

24 Claims, No Drawings

FLUORIDE PREPARATIONS CONTAINING SURFACE-ACTIVE AGENTS

BACKGROUND OF THE INVENTION

Various fluoride compounds have been suggested and used in compositions used in the oral cavity, such as toothpaste, mouthwash or solutions for professional application, to inhibit dental caries (see, for example, U.S. Pat. Nos. 3,029,191 and 4,078,053). One of the purposes of the use of fluoride compounds, such as ammonium, sodium and potassium fluoride, has been to form fluorapatite. Formation of fluorapatite has been achieved by adding orthophosphate to slightly acidic fluoride preparations (see Brudevold et al., Archs Oral Biol., 8: 167–177, 1963), using monofluorophosphate preparations (see Ericsson, Acta Odont Scand., 21: 341–358, 1963), or by increasing the time of application of treatment, and by other techniques. However, the monofluorophosphate application leads to extremely limited fluorapatite formation (see Gron and Caslavsky, Caries Res., 15: 90–97, 1981), while application of fluoride preparations for a long period of time often is not practical.

Past work on the effect of surface-active agents on enamel fluoride interactions has been limited to consideration of the types of agents which are incorporated into dentifrices. Thus, Volker et al. (J. Dent Res., 22: 228, 1943) found that fluoride was readily adsorbed onto powdered enamel from fluoride solutions containing alkyl sulfate without surface-active agents, although the adsorption was not quite so great as that found in aqueous solutions, alone. Massler (J. Dent. Res., 32: 703, 1953) found some reduction in the protection against acid dissolution imparted to enamel from topical fluoride application, if the treatment solution contained detergents. While detergents are present in a number of fluoride rinses (Accepted Dental Therapeutics, 1977) and toothpaste compositions, the reason has not been therapeutic, but rather to keep flavoring oils and other nonsoluble or dispersed additives in suspension.

SUMMARY OF THE INVENTION

This invention relates to fluoride-containing compositions useful in inhibiting or preventing dental caries and to such compositions which contain surface-active agents, to increase fluorapatite formation from fluoride-enamel interactions, and to the use of such compositions in the oral cavity.

It has been discovered that the addition of certain surfactants to dental fluoride compositions greatly and unexpectedly enhances fluorapatite formation from fluoride-enamel interaction. In particular, the use of surfactants, which provide for low surface tensions; for example, less than 40 dynes/cm; for example, less than 30 dynes/cm, in aqueous solutions at low concentrations; for example, 0.001% at 20° C. in deionized water, considerably increases fluorapatite formation, when the resulting compositions are employed in the oral cavity. More particularly, it has been found that surfactants, having a perfluoroalkyl group, are specific surfactants useful in the invention, alone or in combination with phosphate additives.

The fluoride compositions of the invention include, but are not limited to: liquids, creams, rinses, gels, pastes, solutions, chewing gums, lozenges, powders or other suitable compositions. The fluoride of the compositions may vary and be used alone or in combination with other fluorides or other additives. Typical fluoride compounds as active ingredients include, but are not limited to: ammonium fluoride, alkali metal fluoride, such as sodium and potassium fluoride, and other mild fluorides, such as stannous fluoride and combinations thereof. The concentration of the fluoride may vary; for example, 5 to 30000 ppm, such as 50 to 19000 ppm. Other additives which are often employed comprise polishing agents, binders, humectants, gelling agents, preservatives, sweetening agents, dyes, flavoring agents and oils, solvents, such as ethanols and glycols, phosphates, buffers, emulsifiers, as well as other surfactants, alone or in combination.

Specific surfactants suitable for use in combination with fluoride, to increase fluorapatite formation, comprise fluorochemical surfactants and surfactant-synergist systems commercially sold under the trademark Lodyne (a trademark of Ciba-Geigy Company). The fluoroalkyl surfactants have a structure $R_f$—A—Z, wherein $R_f$ represents a hydrophobic and oleophobic linear perfluoroalkyl group $CF_3(CF_2)_n$—, wherein n is 5 to 11 and wherein A represents a hydrocarbon linking group and Z represents the hydrophilic portion of the surfactant. Fluoroamide synergists may be used to further reduce the surface tension of the surfactants. Typical surfactants include, but are not limited to: fluoroalkyl amino carboxylic acid, fluoroalkyl sodium sulfonate, fluoroalkyl ammonium chloride, fluoroalkyl polyoxyethylene, fluoroalkyl amino carboxylic acid and fluoroalkyl amide, and fluoroalkyl sodium sulfonate and fluoroalkyl amide. The surfactants are described more particularly in U.S. Pat. Nos. 4,014,926; 4,069,244; 4,081,399; and 4,089,804. The surfactants are employed in a concentration sufficient to enhance fluorapatite formation, and typically in amounts of from 0.001% to 3.0% by weight of the fluoride compound, such as 0.1% to 1.0%. The fluoroalkyl surfactants, which exhibit amphoteric ionic character and cause 30 to 16 dynes/cm surface tension in deionized water at 25° C. over the concentration of 0.001% to 0.1%, are most desirable. In one preferred embodiment, the use of the fluoroalkyl amino carboxylic acid surfactant, in combination with fluoroalkyl amide synergists; for example, 10% to 50% of the surfactant, has been found to increase substantially fluorapatite formation from application to enamel of slightly acidic fluoride solutions.

In another embodiment, it has been found that the combination of phosphate compounds, particularly the ammonium and alkali metal phosphates, such as orthophosphate and monofluorophosphate, with the fluoride composition and the selected surfactant, substantially increases fluorapatite formation, particularly from application of slightly acidic compositions; for example, a pH of about 5.0 to 6.5; however, the pH range of the composition may vary from 3.0 to 8.5. Orthophosphates and monofluorophosphates have been added to fluoride solutions, to minimize enamel dissolution, without jeopardizing fluorapatite formation. However, prolonged reaction times; for example, over 1 to 2 hours or more, are required, to achieve material fluorapatite formation in depth into the tooth enamel. In combination with the fluoride-surfactant ingredients, these phosphate compounds significantly increase fluorapatite formation. In the preferred embodiment illustrated, a five-minute topical application of a fluoride solution with orthophosphate and the selected surfactant provides as much fluorapatite formation as a six-hour application without the surfactant. The amount of phosphate compound to be employed may vary, but may range, for example, from 0.01% to 20% of the composition, typically from about 0.02% to 10%, The composition of the invention may comprise mouthwashes or rinses and toothpaste, and representative compositions are as follows:

| Mouthwash or Rinse | |
|---|---|
| Sodium, potassium or ammonium fluoride | 0.05–0.1 parts |
| Ethyl alcohol | 5 to 20 parts |
| Flavoring agent | 0.05 to 2.0 parts |
| Sweetener | 0.001 to 0.05 parts |
| Surfactant | 0.1 to 20 parts |
| Orthophosphate | 0.1 to 50 parts |
| Water | balance to 100 parts |

| Dental Preparation | |
|---|---|
| Sodium, potassium or ammonium fluoride | 0.2 parts |
| Water-insoluble polishing agent; e.g., calcium pyrophosphate | 40 to 80 parts |
| Humectant - glycerin | 20 to 40 parts |
| Thickener | 0.1 to 3.0 parts |
| Sweetener | 0.1 to 1.0 parts |
| Preservative | 0.05 to 1.0 parts |
| Flavoring agent | 0.1 to 1.5 parts |
| Water | balance to 100 parts |

The invention will be described for the purpose of illustration only in connection with certain embodiments. However, various changes and modifications and improvements may be made by those persons skilled in the art, all without departing from the spirit and scope of the invention.

DESCRIPTION OF THE EMBODIMENTS

Example 1

Enamel blocks were imbibed in 0.1% solutions of various surface-active agents for 24 hours, and then a 5-minute application of 1.5 M KF at natural pH of 8.5 was applied. Six consecutive layers of enamel were etched off, and the fluoride concentration was determined at 2.5, 5, 10 and 20 μm by interpolation. The surface-active agents are listed in their ability to increase fluoride concentration at the 10 μm depth in the following Table I.

TABLE I

Fluoride deposition in enamel imbibed in 0.1% SAA for 24 hours from a 5-minute application of 1.5 M KF, pH 8.5. (SAA: surface-active agent).

| Pretreatment in 0.1% SAA | Immediate total fluoride (ppm) at depth of | | | |
|---|---|---|---|---|
| | 2.5 μm | 5 μm | 10 μm | 20 μm |
| Octyl-β-d-glucopyranoside | 4200 | 980 | 240 | <100 |
| Dodecylamine chloride | 3350 | 1020 | 280 | <100 |
| Aerosol-22[1] | 2840 | 1000 | 335 | <100 |
| Zonyl-FSJ[2] | 2600 | 1200 | 350 | <100 |
| Zonyl-FSA | 2080 | 1000 | 350 | <100 |
| 2-amino-2-methyl 1,3 propandiol | 7100 | 2000 | 570 | 200 |
| Zonyl FSN | 3700 | 1500 | 430 | 100 |
| Tween-20[3] | 3230 | 1320 | 450 | 130 |
| $H_2O$ | 2350 | 1400 | 480 | <100 |
| Triton X-100[4] | 4000 | 1450 | 500 | 140 |
| Zwittergent 308[5] | 4300 | 1650 | 520 | 175 |
| Lodyne S-110[6] | 4350 | 1300 | 530 | 200 |
| NCS | 4800 | 1640 | 545 | 120 |
| Ethanol | 7100 | 2000 | 570 | 200 |

TABLE I-continued

Fluoride deposition in enamel imbibed in 0.1% SAA for 24 hours from a 5-minute application of 1.5 M KF, pH 8.5. (SAA: surface-active agent).

| Pretreatment in 0.1% SAA | Immediate total fluoride (ppm) at depth of | | | |
|---|---|---|---|---|
| | 2.5 μm | 5 μm | 10 μm | 20 μm |
| Zonyl FSP | 5060 | 1530 | 575 | 140 |
| Cepacol[7] | 4200 | 1050 | 610 | 365 |
| Dodecyl-β-maltoside | 3000 | 1250 | 620 | 215 |
| Lodyne S-112 | 3750 | 1900 | 660 | 110 |
| Triton X-405 | 4250 | 1800 | 700 | 190 |
| Zonyl FSB | 3950 | 1700 | 790 | 230 |
| Lodyne S-107 | 4600 | 2000 | 800 | 260 |
| Zonyl FSC | 4500 | 1950 | 1080 | 340 |
| Zwittergent 310 | 4080 | 2200 | 1130 | 660 |
| Cetyl pyridinium Cl | 4500 | 2200 | 1300 | 130 |
| Decyl-β-d-glucopyranoside | 6400 | 3350 | 1740 | 685 |
| Zwittergent 316 | 20000 | 5300 | 2650 | 1220 |
| Lodyne S-110 | 6200 | 2260 | 2730 | 375 |

[1]Aerosol is a trademark of American Cyanamide Co.
[2]Zonyl is a trademark of E.I. du Pont de Nemours & Co.
[3]Tween is a trademark of ICI United States Inc. for polyoxyethylene derivatives of partial esters of sorbitol anhydride.
[4]Triton is a trademark of Rohm & Haas Co. for nonionic alkylaryl polyether alcohols.
[5]Zwittergent is a trademark of Calbiochem - Behring Co. for sulfobetain-type surfactants
[6]Lodyne is a trademark of the Ciba-Geigy Corp.
[7]Cepacol is a trademark of Richardson Merrill Co. for a cetyl pyridinium chloride solution The Lodyne surfactants contain a hydrophobic perfluoroalkyl linear chain connected with a hydrocarbon group to the hydrophilic portion of the surfactant and formulated as solutions which can be diluted directly with water. The Lodyne S-110 contains 35% of an amphoteric fluoroalkyl amino carboxylic acid and a nonionic synergist in the form of fluoroalkylamide. The pH of its 1% solution in water is between 6.5 and 8.5, and the concentration of free fluoride in such solution was found to be less than 25 ppm. The Lodyne surfactants may be combined with other hydrocarbon surfactants or with water-miscible cosolvents, to ensure long-term stability and prevent precipitation.

Example 2

The surface-active agents (1%) were added to 1.5 M KF, 1.5 M $KH_2PO_4$, pH 5.0 solutions. Enamel blocks were treated for 5 minutes and then incubated for 24 hours at 100% humidity at 37° C., followed by equilibration against 1 N KOH for 24 hours. Six consecutive layers were etched off, and the fluoride concentration was determined at 2.5, 5, 10 and 20 μm by interpolation. The agents were arranged on the basis of decreasing fluoride concentration at 10 μm depth, and the nine agents showing the highest concentration are listed in Table II.

TABLE II

Fluorapatite formation from a 5-minute application of 1.5 M KF, 1.5 M $KH_2PO_4$, pH 5.0, 24-hour incubation, then KOH equilibration

| Surface-active agent 1% | Firmly bound fluoride (ppm) at depth of | | | |
|---|---|---|---|---|
| | 2.5 μm | 5 μm | 10 μm | 20 μm |
| Lodyne S-110 | 1560 | 1150 | 830 | 285 |
| Zwittergent 310 | 830 | 650 | 725 | 250 |
| Zonyl FSN | 875 | 855 | 635 | 125 |
| Triton X-110 | 870 | 900 | 575 | <100 |
| NCS solubilizer | 930 | 700 | 505 | <100 |
| Zonyl FSC | 1110 | 1535 | 480 | 220 |
| Dodecyl-β-maltoside | 975 | 770 | 460 | 110 |
| Zonyl FSP | 785 | 625 | 460 | 100 |
| Cetyl pyridinium-Cl | 845 | 700 | 450 | 130 |

TABLE II-continued

Fluorapatite formation from a 5-minute application of 1.5 M KF, 1.5 M KH$_2$PO$_4$, pH 5.0, 24-hour incubation, then KOH equilibration

| Surface-active agent | Firmly bound fluoride (ppm) at depth of | | | |
|---|---|---|---|---|
| 1% | 2.5 μm | 5 μm | 10 μm | 20 μm |
| none (control) | 780 | 570 | 350 | 125 |

Example 3

Fluoride penetration in enamel from a 5-minute application of a neutral 1.5 M KF solution with orthophosphate and the fluoroalkyl surfactant alone were determined, and the results are shown in Table III.

TABLE III

Immediate fluoride penetration in enamel after a 5-minute application of neutral 1.5 M KF

| Agent added to KF | Mean fluoride concentration (ppm ± SE) at | | | |
|---|---|---|---|---|
|  | 2.5 μm | 5 μm | 10 μm | 20 μm |
| none | 8650 | 5600 | 2170 | 485 |
|  | ±450 | ±505 | ±310 | ±110 |
| 1.5 M orthophosphate | 3450 | 1830 | 720 | 140 |
|  | ±150 | ±90 | ±120 | ±30 |
| 1% cetyl pyridinium-Cl | 9450 | 5300 | 1370 | 360 |
|  | ±2150 | ±990 | ±240 | ±125 |
| 1% Lodyne S-110 | 5525 | 1450 | 310 | <100 |
|  | ±365 | ±275 | ±40 |  |

The addition of orthophosphate reduces penetration of fluoride, as may be seen, for example, in column 3 at the 10 μm depth, comparing the 720 ppm fluoride concentration with the 2170 ppm concentration. The Lodyne S-110 surfactant markedly affects fluoride penetration, the respective fluoride concentration being 2170 ppm and 310 ppm at 10 μm depth.

Example 4

The amount of fluorapatite formation was determined for the neutral formulation of Table III as shown in Table IV.

TABLE IV

Fluorapatite formation in enamel after a 5-minute application of neutral 1.5 M KF. 24-hour incubation before KOH equilibration

| Agent added to KF | Mean fluoride concentration (ppm ± SE) at | | | |
|---|---|---|---|---|
|  | 2.5 μm | 5 μm | 10 μm | 20 μm |
| none | 365 | 315 | 265 | <100 |
|  | ±65 | ±50 | ±60 |  |
| 1.5 M orthophosphate | 660 | 525 | 460 | 295 |
|  | ±20 | ±30 | ±30 | ±40 |
| 1% cetyl pyridinium-Cl | 690 | 570 | 460 | 170 |
|  | ±65 | ±60 | ±35 | ±10 |
| 1% Lodyne S-110 | 695 | 620 | 550 | 340 |
|  | ±70 | ±65 | ±60 | ±50 |

The fluoroalkyl surfactant increased the amount of fluorapatite formation in the enamel.

Example 5

Comparative data, similar to Tables III and IV, were determined for a slightly acidic fluoride preparation, and the results are shown in Tables V and VI.

TABLE V

Immediate fluoride penetration in enamel after a 5-minute application of 1.5 M KF, pH 5.0

| Agent added to KF | Mean fluoride concentration (ppm ± SE) at | | | |
|---|---|---|---|---|
|  | 2.5 μm | 5 μm | 10 μm | 20 μm |
| none | 21100 | 15500 | 7580 | 1070 |
|  | ±3600 | ±2700 | ±1140 | ±140 |
| 1.5 M orthophosphate | 12800 | 5400 | 1550 | 450 |
|  | ±680 | ±720 | ±220 | ±70 |
| 1% cetyl pyridinium-Cl | 6000 | 3640 | 1370 | 150 |
|  | ±1090 | ±500 | ±330 | ±30 |
| 1% Lodyne S-110 | 10100 | 8500 | 4600 | 745 |
|  | ±570 | ±560 | ±380 | ±120 |

TABLE VI

Fluorapatite formation in enamel after a 5-minute application of 1.5 M KF, pH 5.0. 24-hour incubation before KOH equilibration

| Agent added to KF | Mean fluoride concentration (ppm ± SE) at | | | |
|---|---|---|---|---|
|  | 2.5 μm | 5 μm | 10 μm | 20 μm |
| none | 820 | 670 | 450 | 240 |
|  | ±110 | ±90 | ±50 | ±40 |
| 1.5 M orthophosphate | 780 | 570 | 350 | 125 |
|  | ±100 | ±70 | ±55 | ±30 |
| 1% cetyl pyridinium-Cl | 845 | 700 | 450 | 130 |
|  | ±40 | ±30 | ±5 | ±15 |
| 1% Lodyne S-110 | 1060 | 880 | 730 | 485 |
|  | ±45 | ±20 | ±30 | ±15 |

In Table V, it may be noted that cetyl pyridinium chloride at this pH is more effective in reducing fluoride penetration than orthophosphate, while Lodyne S-110 is less effective than orthophosphate.

In Table VI, the data on fluorapatite formation from 1.5 M potassium fluoride pH 5 solution show that cetyl pyridinium chloride had no effect at this pH, while Lodyne S-110 greatly enhanced fluoroapatite formation at all depths.

Example 6

The fluoroalkyl surfactant was then tested in combination with orthophosphate, and the data are shown in Table VII.

TABLE VII

Fluorapatite formation in enamel after a 5-minute application of 1.5 M KF, pH 5.0. 24-hour incubation before KOH equilibration

| Agent added to KF | Mean fluoride concentration (ppm ± SE) at | | | |
|---|---|---|---|---|
|  | 2.5 μm | 5 μm | 10 μm | 20 μm |
| none | 820 | 670 | 450 | 240 |
|  | ±110 | ±90 | ±50 | ±40 |
| 1.5 M orthophosphate | 780 | 570 | 350 | 125 |
|  | ±100 | ±70 | ±50 | ±30 |
| 1% Lodyne S-110 | 1060 | 880 | 730 | 485 |
|  | ±45 | ±20 | ±30 | ±15 |
| 1% Lodyne S-110 1.5 M orthophosphate | 1560 | 1250 | 930 | 520 |
|  | ±65 | ±55 | ±60 | ±65 |

Significantly more fluorapatite was formed at any depth by this combination. The findings compare favorably with those from several 6-hour applications. It should be noted that the increased fluoroapatite formation occurs while calcium fluoride formation appears to be depressed, judging from the data on fluoride penetration. The data suggest an unexpected additive effect of phosphate and Lodyne on fluorapatite formation, particularly at a slightly acidic pH. The data establish that fluoroalkyl surface-active agents in the enamel structure, during the treatment and the incubation period, favorably affect fluorapatite formation.

What is claimed is:

1. A composition for use in the oral cavity to increase fluorapatite formation in teeth enamel, which composition comprises:
   (a) a dental-caries-inhibiting amount of a water-soluble fluoride compound; and
   (b) a fluoroalkyl surfactant in an amount to increase the fluorapatite formation of the teeth enamel, the surfactant having the structure $R_f-A-Z$, wherein $R_f$ represents a perfluoroalkyl group having the formula $CF_3(CF_2)_n-$, wherein n is 5 to 11, A represents a hydrocarbon linking group and Z represents a hydrophilic group.

2. The composition of claim 1 wherein the fluoride compound is selected from the group of ammonium fluoride, sodium flouride, potassium fluoride, stannous fluoride and combinations thereof.

3. The composition of claim 1 wherein the fluoroalkyl surfactant provides a surface tension of less than 30 dynes/cm in deionized water at 25° C. at a concentration of from 0.001% to 0.1%.

4. The composition of claim 1 wherein the fluoroalkyl surfactant is selected from the group of fluoroalkyl amino carboxylic acid, fluoroalkyl sodium sulfonate, fluoroalkyl ammonium chloride, fluoroalkyl polyoxyethylene, fluoroalkyl amino carboxylic acid and fluoroalkyl amide, and fluoroalkyl sodium sulfonate and fluoroalkyl amide.

5. The composition of claim 1 wherein the fluoride is present in an amount of from 50 to 20000 ppm.

6. The composition of claim 1 wherein the fluoroalkyl surfactant is present in an amount of from about 0.001% to 10%.

7. The composition of claim 1 which includes a fluorapatite-increasing amount of a phosphate compound.

8. The composition of claim 7 wherein the phosphate compound comprises a water-soluble orthophosphate compound.

9. The composition of claim 1 which includes a synergistic amount of a fluoroalkyl amide compound.

10. The composition of claim 1 wherein the composition has a pH of from about 3.0 to 8.5.

11. The composition of claim 1 which includes an alkali metal orthophosphate in an amount of from about 0.1% to 40%, and the surfactant comprises a fluoroalkyl amino carboxylic acid surfactant with a synergistic amount of a fluoroalkyl amide, the composition having a slightly acidic pH.

12. A composition for use in the oral cavity to increase fluorapatite formation in teeth enamel, the composition having a pH of from about 3.0 to 8.5, which composition comprises:
   (a) a dental-caries-inhibiting amount of a water-soluble fluoride compound present in an amount of from 50 to 1000 ppm;
   (b) a phosphate compound comprising a water-soluble orthophosphate compound; and
   (c) a fluoroalkyl amino carboxylic acid surfactant present in an amount of from about 0.001% to 1%, to increase the fluorapatite formation of the teeth enamel.

13. The composition of claim 7 wherein the amount of the phosphate compound ranges from about 0.01% to 20% by weight of the composition.

14. The composition of claim 7 wherein the pH of the composition ranges from about 5.0 to 6.5.

15. The composition of claim 9 wherein the synergistic amount of the fluoroalkyl amide compound ranges from about 10% to 50% of the surfactant.

16. The composition of claim 12 which includes a synergistic amount of from about 10% to 50% of the surfactant of a fluoroalkyl amide compound.

17. The composition of claim 12 wherein the pH of the composition ranges from about 5.0 to 6.5.

18. The composition of claim 12 wherein the orthophosphate compound ranges from about 0.01% to 20% by weight of the composition.

19. A method of increasing the amount of fluorapatite formation from fluoride-enamel interaction in the oral cavity, which method comprises introducing into the oral cavity and into contact with the enamel of the teeth in the oral cavity an effective amount of a composition, which composition comprises:
   (a) a dental-caries-inhibiting amount of a water-soluble fluoride compound; and
   (b) a fluoroalkyl surfactant in an amount to increase the fluorapatite formation of the teeth enamel, the surfactant having the structure $R_f-A-Z$, wherein $R_f$ represents a perfluoroalkyl group having the formula $CF_3(CF_2)_n-$, wherein n is 5 to 11, A represents a hydrocarbon linking group and Z represents a hydrophilic group.

20. The method of claim 19 which includes a fluorapatite-increasing amount of a phosphate compound.

21. The method of claim 19 wherein the phosphate compound comprises a water-soluble orthophosphate compound.

22. The method of claim 19 which includes a synergistic amount of a fluoroalkyl amide compound.

23. The method of claim 19 wherein the fluoroalkyl surfactant is selected from the group of fluoroalkyl amino carboxylic acid, fluoroalkyl sodium sulfonate, fluoroalkyl ammonium chloride, fluoroalkyl polyoxyethylene, fluoroalkyl amino carboxylic acid and fluoroalkyl amide, and fluoroalkyl sodium sulfonate and fluoroalkyl amide.

24. A solution for use as a mouthwash or mouth-rinse in the oral cavity, which solution comprises:
   (a) 0.05 to 0.1 parts of sodium, potassium or ammonium fluoride;
   (b) 5 to 20 parts of ethyl alcohol;
   (c) 0.05 to 2.0 parts of a flavoring agent;
   (d) 0.001 to 0.05 parts of a sweetener;
   (e) 0.1 to 20 parts of a surfactant having the structure $R_f-A-Z$, wherein $R_f$ represents a perfluoroalkyl group having the formula $CF_3(CF_2)_n-$, wherein n is 5 to 11, A represents a hydrocarbon linking group and Z represents a hydrophilic group;
   (f) 0.1 to 50 parts of orthophosphate; and
   (g) the balance to 100 parts of water.

* * * * *